United States Patent
Kleinberg

(10) Patent No.: US 6,563,314 B1
(45) Date of Patent: May 13, 2003

(54) WELL LOGGING METHOD AND APPARATUS FOR DETERMINING THE NUCLEAR MAGNETIC RESONANCE LONGITUDINAL MAGNETIZATION DECAY OF FORMATIONS

(75) Inventor: Robert L. Kleinberg, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 09/247,834

(22) Filed: Feb. 10, 1999

(51) Int. Cl.⁷ .................................................. G01V 3/00
(52) U.S. Cl. ..................................... 324/303; 324/318
(58) Field of Search ................................ 324/303, 318, 324/322, 319, 306, 307, 309, 300

(56) References Cited

U.S. PATENT DOCUMENTS

| | | | |
|---|---|---|---|
| 3,597,681 A | 8/1971 | Huckabay et al. | 324/5 R |
| 3,617,867 A | 11/1971 | Herzog | 324/5 |
| 3,667,035 A * | 5/1972 | Slichter | 324/303 |
| 4,350,955 A | 9/1982 | Jackson et al. | 324/303 |
| 4,777,443 A | 10/1988 | Yabusaki et al. | 324/322 |
| 4,987,368 A | 1/1991 | Vinegar | 324/303 |
| 5,023,551 A | 6/1991 | Kleinberg et al. | 324/303 |
| 5,055,787 A | 10/1991 | Kleinberg et al. | 324/303 |
| 5,153,514 A | 10/1992 | Griffin et al. | 324/303 |
| 5,247,256 A | 9/1993 | Marek | 324/321 |
| 5,254,950 A | 10/1993 | Fan et al. | 324/322 |
| 5,258,710 A | 11/1993 | Black et al. | 324/309 |
| 5,432,446 A * | 7/1995 | MacInnis et al. | 324/303 |
| 5,508,613 A | 4/1996 | Kotsubo et al. | 324/318 |
| 5,539,309 A * | 7/1996 | Van Wyk et al. | 324/307 |

OTHER PUBLICATIONS

Carr et al., Phys. Rev. 94, 630 (1954).
J. Jackson, New NMR Well Logging Fracture Mapping Technique With Possible Application Of SQUID NMR Detection, Soc. Of Explor. Geo., Tulsa, OK, pp. 161–165, 1981.
Sager, Kleinberg, and Wheatley, Phys. Rev. Lett., 39, 1345 (1977).
Sager, Kleinberg, and Wheatley, J. Low Temp. Phys. 32, 263 (1978).
D.P. Gallegos and D.M. Smith, "A NMR Technique For The Analysis Of Pore Structure", Journal Of Colloid And Interface Science, 122, 143–153 (1988).

(List continued on next page.)

Primary Examiner—Louis Arana
(74) Attorney, Agent, or Firm—Martin M. Novack; Jody L. DeStefanis; William B. Batzer

(57) ABSTRACT

A method for determining the nuclear magnetic resonance longitudinal magnetization decay of formations surrounding an earth borehole that involves: providing a logging device moveable through the borehole; applying a static magnetic field in the formations to align spins in the formations in the direction of the static magnetic field; producing a tipping pulse for tipping the direction of the spins with respect to the static magnetic field direction; and detecting the time varying magnitude of the spin magnetization as the magnetization returns toward the static magnetic field direction; the longitudinal magnetization decay being determinable from the detected time varying magnitude of the spin magnetization. Related methods and apparatus for implementing these methods are also described.

55 Claims, 7 Drawing Sheets

OTHER PUBLICATIONS

Webb, Kleinberg, Wheatley, Phys. Rev. Lett. 33, 145 (1974).
Abragam, Nuclear Magnetism, Oxford, 1982, pp. 254–255.
Giffard, Webb, Wheatley, J. Low Temp. Phys. 6, 533, (1972).
Gallop, Petley, J. Phys E. 9, 417 (1976).
Hilbert, Clarke, Appl. Phys. Lett. 43, 694 (1983).
Hilbert, Clarke, J. Low Temp. Phys. 61, 263 (1985).
Muhlfelder, Beall, Cromar, Ono, Appl. Phys. Lett. 49, 1118 (1986).
Van Harlingen, Koch, Clarke, Appl. Phys. Lett. 41, 197 (1982).
Webb, Rev. Sci. Instr. 48, 1585 (1977).
Kenyon, Day, Straley, Willemsen, SPE 1543.
Encyclopedia Of Nuclear Magnetic Resonance, Edited by D.M. Grant et al., John Wiley, 1996 pp. 4559–4560.
Greenberg, "Application Of Superconducting Quantum Interference Devices To Nuclear Magnetic Resonance", Rev. Mod. Phys., Jan. 1998, pp. 172–222.

Advances In Magnetic And Optical Resonance, Edited by W. Warren, Academic Press, 1990, pp. 201, 222–236 (C. Conner—Low Frequency Magnetic Resonance With a DC Squid).

R.L. Kleinberg et al., Nuclear Magnetic Resonance of Rocks: $T_1$ vs. $T_2$, SPE 26470, 1993, pp. 553–563.

R.L. Kleinberg et al., NMR Properties Of Reservoir Fluids, The Log Analyst, 1996, pp. 20–32.

Clarke et al., The Impact Of High–Temperature Superconductivity On SQUID Magnetometers, Science, Oct. 14, 1988, pp. 217–223.

Murphy, NMR Logging And Core Analysis—Simplified, World Oil, Apr., 1995, pp. 65–70.

Encyclopedia Of Nuclear Magnetic Resonance, Kleinberg, Instrumentation For Well Logging, 1996, pp. 4964–4965.

* cited by examiner

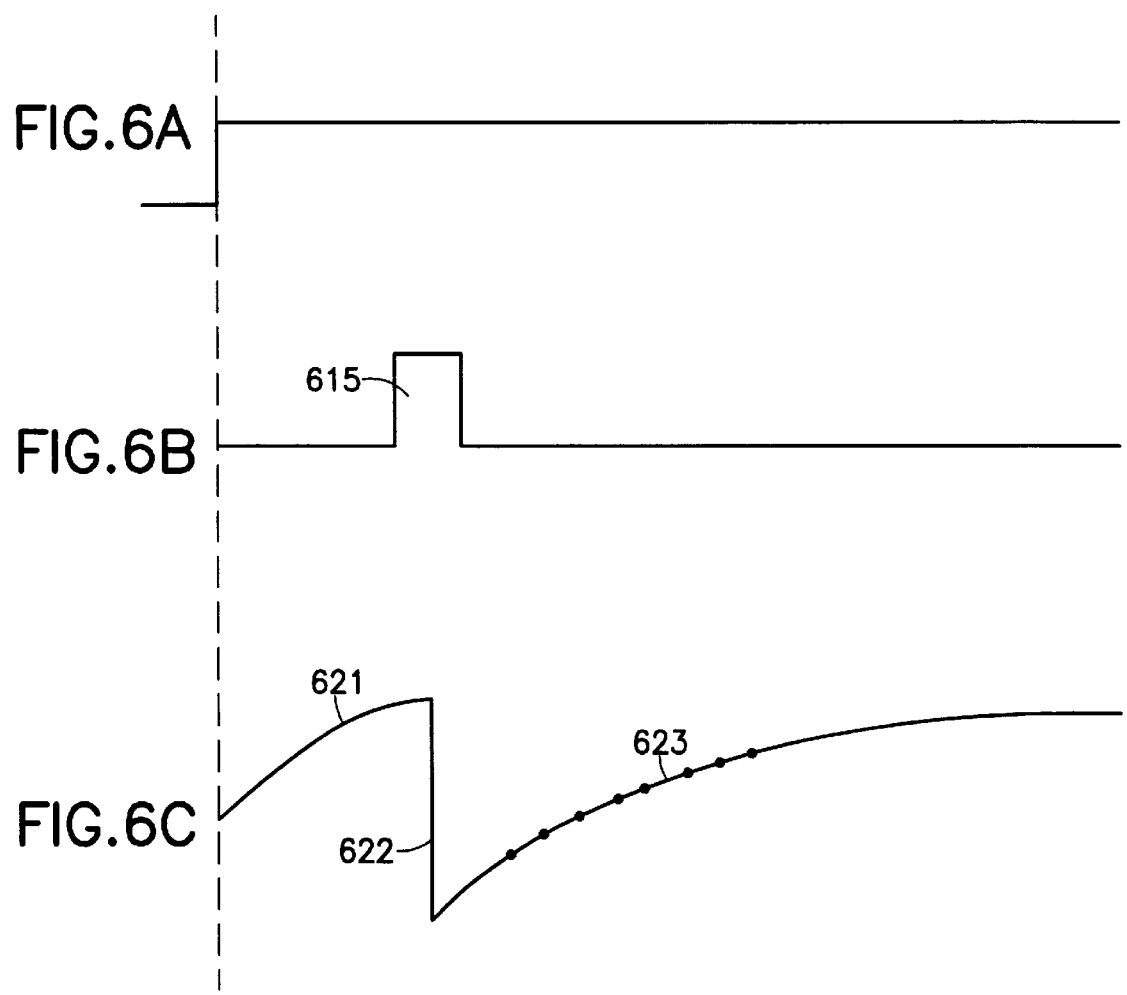

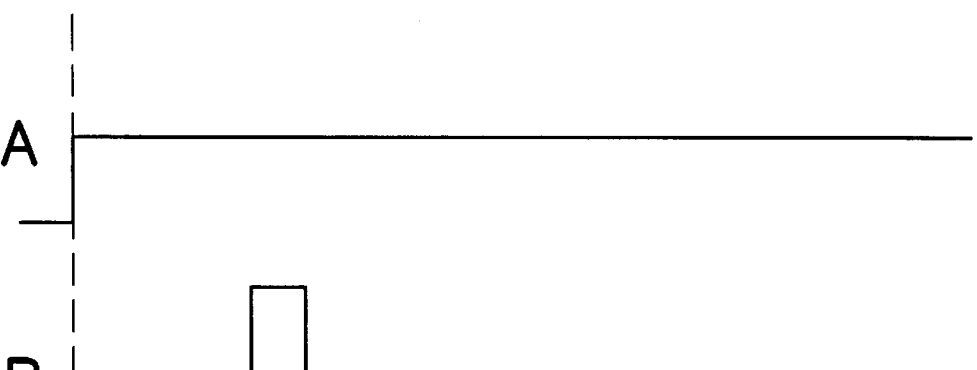
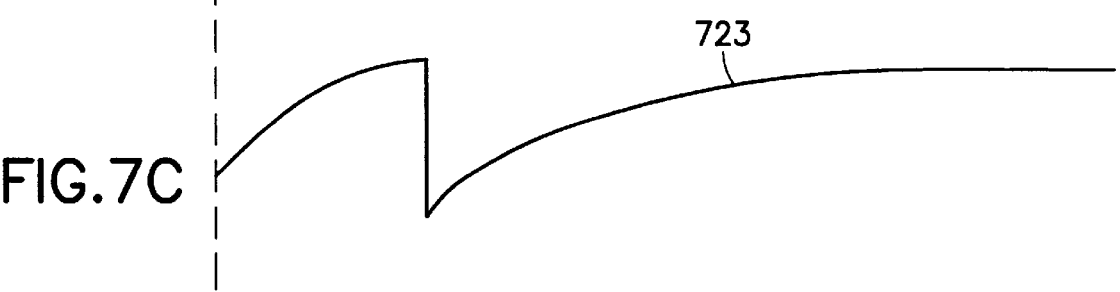
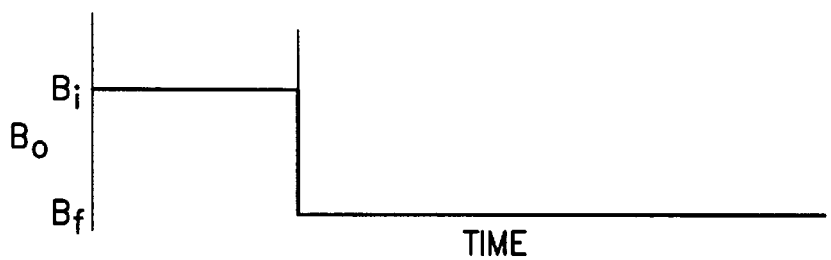
FIG.8A
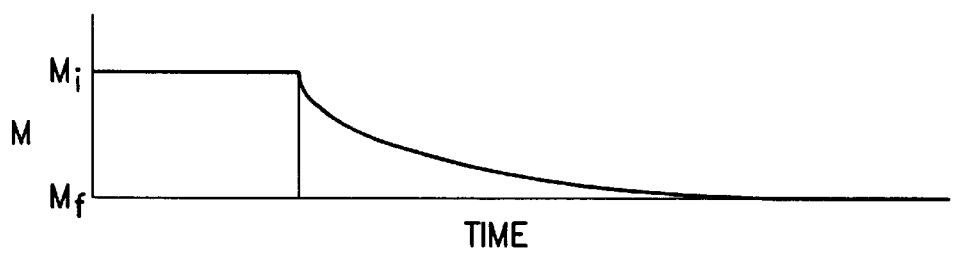
FIG.8B

WELL LOGGING METHOD AND APPARATUS FOR DETERMINING THE NUCLEAR MAGNETIC RESONANCE LONGITUDINAL MAGNETIZATION DECAY OF FORMATIONS

FIELD OF THE INVENTION

This invention relates to determination of nuclear magnetic resonance properties of formations surrounding an earth borehole and, more particulary, to a well logging method and apparatus for determining the nuclear magnetic resonance longitudinal magnetization decay of formations surrounding an earth borehole.

The longitudinal relaxation time constant of the formations, and/or the distribution thereof, can be obtained from the longitudinal magnetization decay.

BACKGROUND OF THE INVENTION

General background of nuclear magnetic resonance (NMR) well logging is set forth, for example, in U.S. Pat. No. 5,023,551. Briefly, in conventional NMR operation the spins of nuclei align themselves along an externally applied static magnetic field. This equilibrium situation can be disturbed by a pulse of an oscillating magnetic field (e.g. an RF pulse), which tips the spins away from the static field direction. After tipping, two things occur simultaneously. First, the spins precess around the static field at the Larmor frequency, given by $\omega_0 = \gamma B_0$, where $B_0$ is the strength of the static field and $\gamma$ is the gyromagnetic ratio. Second, the spins return to the equilibrium direction according to a decay time T1, which is called the longitudinal relaxation time constant or spin lattice relaxation time constant. For hydrogen nuclei, $\gamma/2\pi = 4258$ Hz/Gauss, so, for example, for a static field of 235 Gauss, the frequency of precession would be 1 MHz. Also associated with the spin of molecular nuclei is a second relaxation time constant, T2, called the transverse relaxation time constant or spin-spin relaxation time constant. At the end of a ninety degree tipping pulse, all the spins are pointed in a common direction perpendicular to the static field, and they all precess at the Larmor frequency. The net precessing magnetization decays with a time constant T2 because the individual spins rotate at different rates and lose their common phase. At the molecular level, dephasing is caused by random motions of the spins. The magnetic fields of neighboring spins and nearby paramagnetic centers appear as randomly fluctuating magnetic fields to the spins in random motion. In an inhomogeneous field, spins at different locations precess at different rates. Therefore, in addition to the molecular spin-spin relaxation of fluids, spatial inhomogeneities of the applied field also cause dephasing. Spatial inhomogeneities in the field can be due to microscopic inhomogeneities in the magnetic susceptibility of rock grains or due to the macroscopic features of the magnet.

A widely used technique for acquiring NMR data, both in the laboratory and in well logging, uses an RF pulse sequence known as the CPMG (Carr-Purcell-Meiboom-Gill) sequence. As is well known, after a wait time that precedes each pulse sequence, a ninety degree pulse causes the spins to start precessing. Then a one hundred eighty degree pulse is applied to cause the spins which are dephasing in the transverse plane to refocus. By repeatedly refocusing the spins using one hundred eighty degree pulses, a series of "spin echoes" appear, and the train of echoes is measured and processed. The transverse relaxation time constant, $T_2$, or the distribution of $T_2$'s, can be obtained using this technique. The determination of the longitudinal magnetization decay and of $T_1$, however, remains difficult. A source of this difficulty is the very low signal-to-noise ratio inherent in detecting the feeble magnetic moment of nuclei.

The traditional pulse method of measuring the longitudinal relaxation time constant ($T_1$) is the so-called inversion recovery method (see Carr et al., Phys. Rev. 94, 630 (1954)). In this method, a 180 degree pulse is applied to a nuclear spin system, followed by a recovery time and then a 90 degree read-out pulse. The amplitude at a convenient point on the resulting free induction decay is measured, and the spin system is then allowed to recover to equilibrium by waiting approximately five times $T_1$ before applying the next two-pulse sequence. Many such cycles are required since the spin-lattice relaxation time is found by correlating the various recovery times with the associated free induction decay (FID) amplitudes. While this technique can provide an accurate measure of $T_1$ (and, with further processing, the $T_1$ distribution), the pulse sequence is very time consuming.

It is among the objects of the present invention to provide an apparatus and method that can determine the longitudinal magnetization decay and relaxation time constant of formations surrounding an earth borehole, with improved time and cost efficiency.

SUMMARY OF THE INVENTION

A form of the present invention provides a well logging technique and apparatus whereby the longitudinal magnetization decay and the longitudinal relaxation time constant ($T_1$) of formations surrounding an earth borehole can be measured directly after a single RF pulse or other suitable perturbation in direction and/or magnitude of the magnetization of the spins. In embodiments of this form of the invention, the longitudinal magnetism (that is, magnetism parallel to the static magnetic field) is sensed, in general, by a magnetic flux detector, and specifically by a superconducting flux detector. SQUIDs are the most sensitive flux detectors, but there are other flux detectors (flux gate magnetometers, conventional coils and amplifiers, etc.) which can, in principle, be used.

Superconductors have been employed in the design of electromagnetic sensors that are extremely sensitive. The heart of a superconducting sensor is the Superconducting Quantum Interferometric Device (SQUID), which can be envisioned as a very sensitive converter of magnetic flux to voltage. Typically, a measurement circuit will be arranged so that the detected signal results in a current flow in a loop that is inductively coupled to the SQUID. SQUIDs do not generate high fields, and they do not carry high currents. They are mechanically robust and compact, and are therefore relatively easy to cool. SQUIDs have been proposed for use in borehole logging but have not become commercially prevalent for a number of reasons, one such reason being the difficulty of devising suitable and practical logging applications for SQUIDs. [See, for example, J. Jackson, New NMR Well Logging/Fracture Mapping Technique With Possible Application Of SQUID NMR Detection, Soc. Of Explor. Geo., Tulsa, Okla., pp. 161–165, 1981.]

In accordance with an embodiment of the method of the invention, there is disclosed a technique for determining the nuclear magnetic resonance longitudinal magnetization decay of formations surrounding an earth borehole, comprising the following steps: providing a logging device that is moveable through the borehole; applying, from the logging device, a static magnetic field in the formations to align spins in the formations in the direction of the static magnetic field; producing, from the logging device, a tipping pulse for tipping the direction of the spins with respect to the static magnetic field direction; and detecting, at the logging device, the time varying magnitude of the spin magnetization as said magnetization returns toward the static magnetic field direction; the longitudinal magnetization decay being determinable from the detected time varying magnitude of the spin magnetization. [As background, see Sager, Kleinberg, and Wheatley, Phys. Rev. Lett., 39, 1345 (1977), and Sager, Kleinberg, and Wheatley, J. Low Temp. Phys. 32, 263 (1978), regarding laboratory application of SQUID detected signals using a 180 degree pulse and monitoring of longitudinal magnetization for NMR investigation of $^3$He.]

In a preferred embodiment of the method of the invention, the step of detecting the time varying magnitude of the spin magnetization includes providing a magnetic flux detection system for producing a number of output signals representative of successively sampled values of the magnetic flux over a period of time. The magnetic flux detection system includes a magnetic flux detection sensor (or antenna), and a magnetic flux sensing circuit that preferably includes a SQUID. In a form of the preferred embodiment, at least part of the magnetic flux detection system is in a cooled enclosure.

In accordance with a feature of an embodiment of the invention, an all-metal pressure-tight housing is provided for the flux detection system. This facilitates thermal shielding (e.g. vacuum dewaring) for cooled components, and is possible because the quasistatic nature of the signal (a few hundred Hertz bandwidth) is below the frequency at which the metal housing becomes opaque to magnetic fields. For higher frequency operation, the portion of the metal housing in front of the flux detection antenna (e.g. receiver coil) can have a reduced wall thickness.

Further features and advantages of the invention will become more readily apparent from the following detailed description when taken in conjunction with the accompanying drawings.

BRIEF DESCRIPTION OF THE DRAWINGS

FIG. 6, which includes FIGS. 6A, 6B and 6C, show plots of magnetization versus time that are useful in understanding operation of an embodiment of the invention.

FIG. 7, which includes FIGS. 7A, 7B and 7C, show other plots of magnetization versus time that are useful in understanding operation of another embodiment of the invention.

FIG. 8, which includes FIGS. 8A and 8B, show further plots of magnetization versus time that are useful in understanding operation of a further embodiment of the invention.

DETAILED DESCRIPTION

Figure 1:
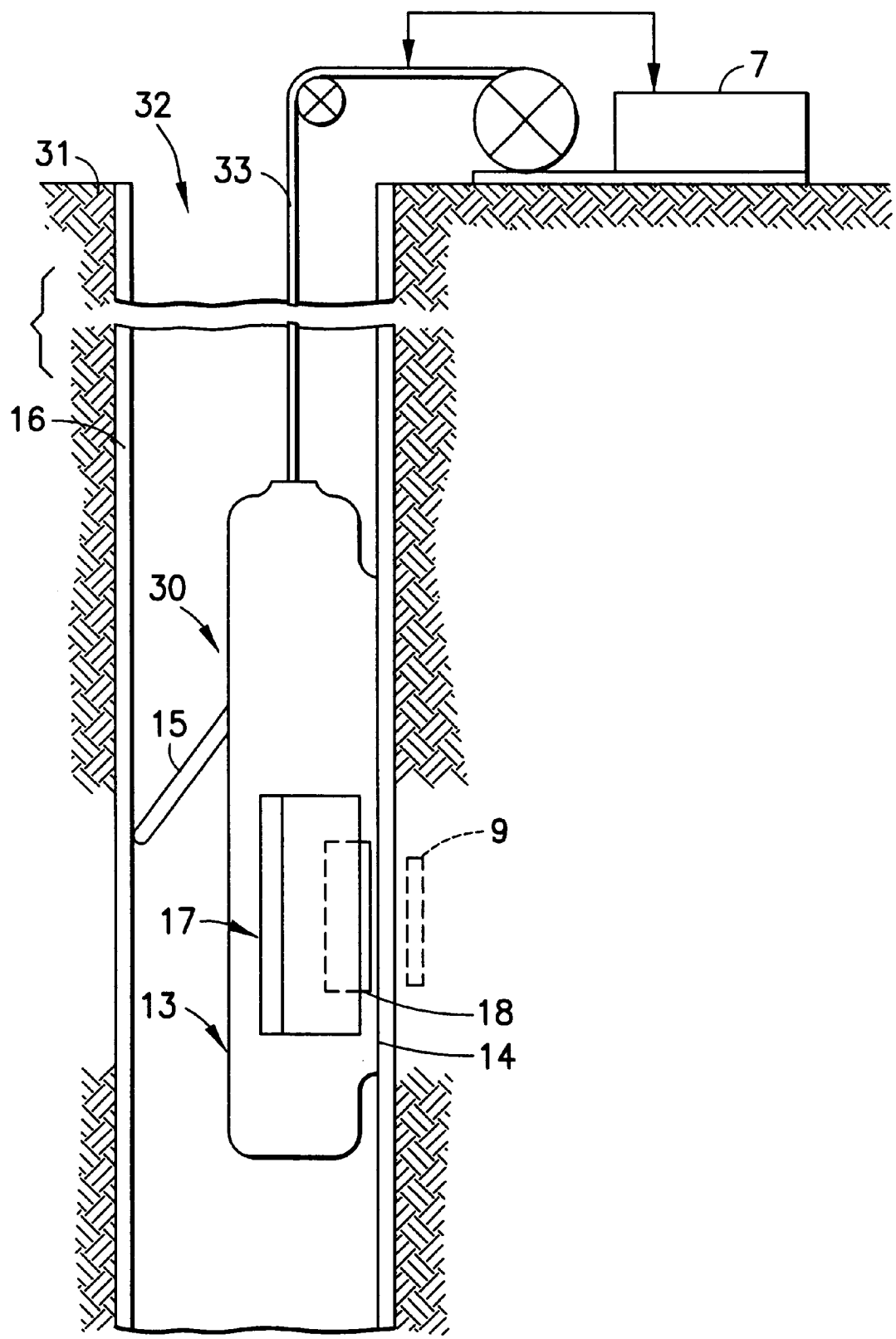
FIG. 1 is a schematic diagram, partially in block form, of an apparatus that can be used in practicing embodiments of the invention.

Referring to FIG. 1, there is shown an apparatus for investigating subsurface formations 31 traversed by a borehole 32, which can be used in practicing embodiments of the invention. A magnetic resonance investigating apparatus or logging device 30 is suspended in the borehole 32 on an armored cable 33, the length of which substantially determines the relative depth of the device 30. The length of cable 33 is controlled by suitable means at the surface such as a drum and winch mechanism (not shown). Surface equipment, represented at 7, can be of conventional type, and can include a processor subsystem and communicates with the all the downhole equipment. It will be understood that processing can be performed downhole and/or uphole, and that some of the processing may be performed at a remote location. Also, while a wireline is illustrated, alternative forms of physical support and communicating link can be used, for example in a measurement while drilling system. As described for example in the U.S. Pat. No. 5,055,787, the magnetic resonance logging device 30 has a face 14 shaped to intimately contact the borehole wall, with minimal gaps or standoff. The borehole wall may have a mudcake 16 thereon. A retractable arm 15 is provided which can be activated to press the body of the tool 13 against the borehole wall during a logging run, with the face 14 pressed against the wall's surface. Although the tool 13 is shown as a single body, the tool may alternatively comprise separate components such as a cartridge, sonde or skid, and the tool may be combinable with other logging tools.

Figure 2:
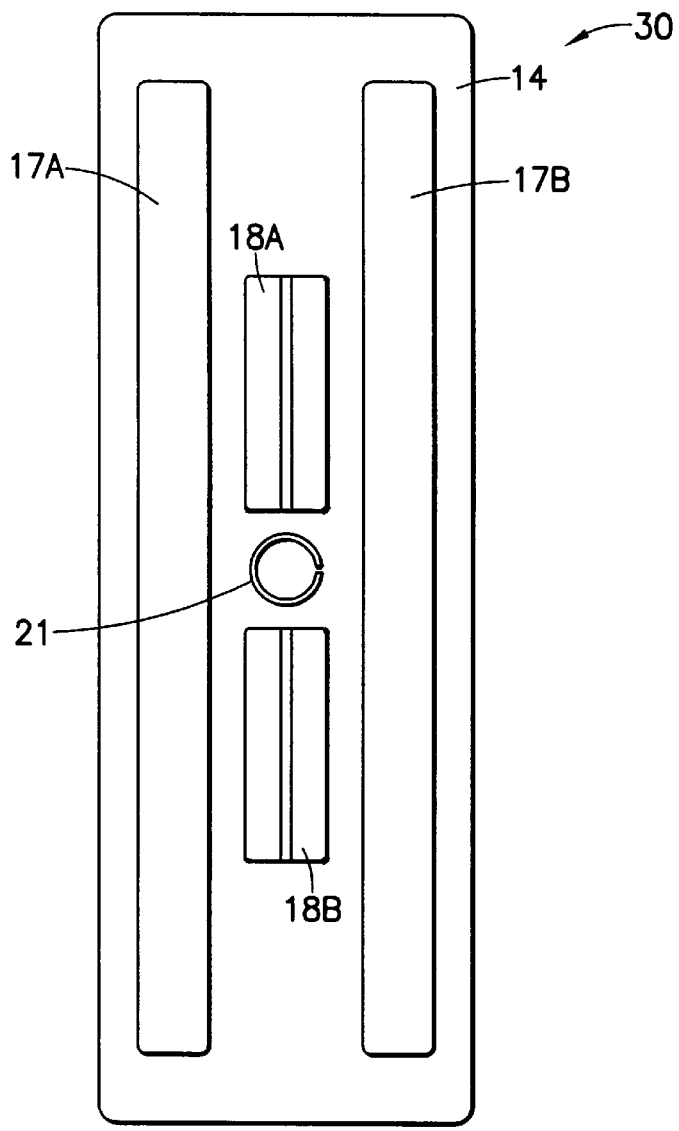
FIG. 2 is a diagram of the front borehole wall-engaging face of an embodiment of the logging device of FIG. 1, which can be used in practicing embodiments of the invention.

The diagram of FIG. 2 shows the front face of the logging device 30 that abuts the borehole wall. In the embodiment of FIG. 2, a pair of spaced-apart permanent magnets 17A and 17B are provided. The magnets can be, for example, samarium-cobalt magnets, and can have the general configuration and polarity as shown in the above-referenced U.S. Pat. No. 5,055,787. A pair of RF antennas 18A and 18B are provided between the permanent magnets 17A and 17B. Each of the RF antennas can have the general type of configuration shown in the above-referenced '787 patent; that is, an elongated trough antenna. However, whereas the '787 patent illustrates one such RF antenna and uses the single RF antenna for both transmitting and receiving, the present embodiment hereof utilizes the two longitudinally aligned and spaced apart RF antennas 18A and. 18B for transmitting RF electromagnetic energy, and utilizes a pick-up loop antenna 21, located between the antennas 18A and 18B, for receiving NMR signals from the formations. [The present invention can also operate with a single transmitting antenna. However, the plurality of transmitting antennas can provide certain operational advantages, to be treated subsequently.] As will be described further hereinbelow, the loop antenna 21 is preferably part of a magnetic flux detection system, at least part of which comprises superconducting components. Magnets 17A and 17B produce a static magnetic field $B_0$ in regions surrounding the tool 13. The antenna(s) 18 produces, at selected times to be described, an oscillating magnetic field $B_1$ which is focussed into formation 12, and is superposed on the static field $B_0$ within those parts of the formation opposite the face 14. The "volume of investigation" of the tool for this embodiment, represented generally by the dashed line region 9 in FIG. 1, is a vertically elongated region directly in front of tool face 14.

As described in the referenced U.S. Pat. No. 5,055,787, the two permanent magnets 17A and 17B can be mounted generally parallel to each other within a metal alloy body, the body being formed of a material having low magnetic permeability, so as to not interfere with the static magnetic field. The magnets 17A and 17B can be slab magnets which are elongated in the longitudinal direction of the borehole. The magnetic poles of each magnet are not on the smallest faces of the slab, commonly viewed as the ends of a bar magnet. Instead, the poles appear on the two opposing edges of the slab magnet. Therefore, within the formation, the magnetic field $B_0$ surrounding the magnets remains fairly constant along the longitudinal direction of the borehole axis. One or more further permanent magnets can also be used in this embodiment.

Figure 3:
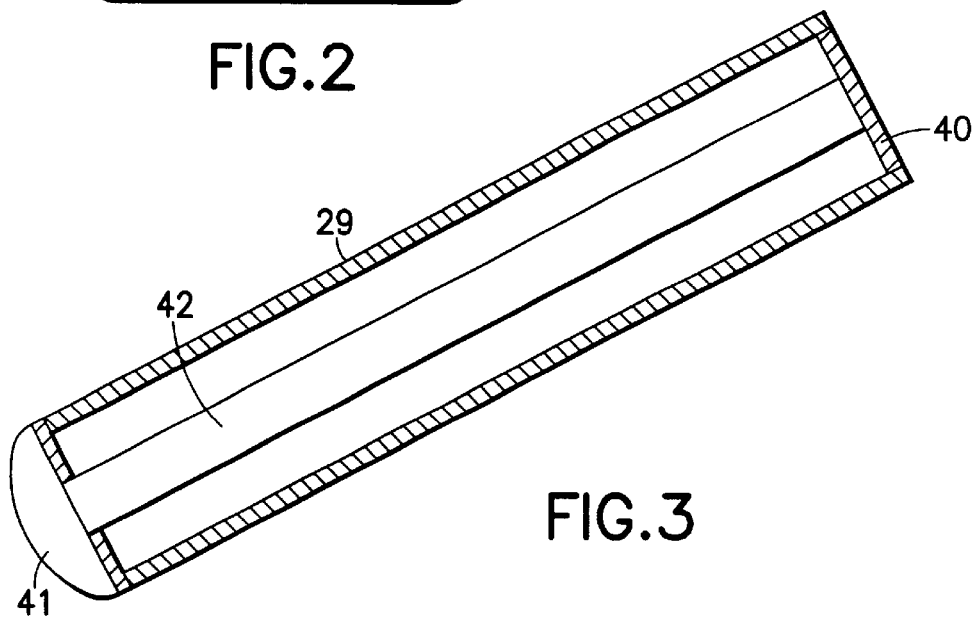
FIG. 3 is a perspective view of an embodiment of one of the RF antennas of the FIG. 2 embodiment.

As described in the referenced '787 patent, the metal body holding the permanent magnets can have, on the front face thereof, a semi-cylindrically shaped cavity or slot which faces the formations and is adapted for receiving an RF antenna (two of them, in this case, as well as the loop antenna 21 therebetween). The antennas 18A and 18B are preferably positioned outside of the metal body of the tool, and are thereby shielded from electromagnetic communication with regions of the borehole which lie behind the metal body or regions of other formations in directions intercepted by the metal body. As illustrated in FIG. 3, the antennas 18A and 18B each have a metal trough-shaped body 29 and an elongated center probe 42, across which signals are applied. Each antenna effectively operates as a current loop which produces an oscillating RF magnetic field $B_1$ that is generally azimuthal in the volume of investigation and substantially perpendicular to the static magnetic field, $B_0$ (which is generally radial in the volume of investigation). The loop 21 has an axis that is generally radial (that is, perpendicular to the longitudinal axis of the logging device and the borehole), and is sensitive to radial signals. The trough-shaped body 29 has end plates 40, 41 with the center conductor or probe 42 extending from one end plate 40 to the other end plate 41, parallel to and centered in the semi-cylindrical trough 29. The U.S. Pat. No. 5,153,514 discloses that the trough antenna, which can be filled with a ferrite, can have an inner conductive shell that is separated from a steel body by a rubber layer, which suppresses magnetoacoustic ringing. It will be understood that various other types of magnetic resonance logging equipment can be used in practicing the invention, a further example being shown in FIG. 8 below.

Figure 4:
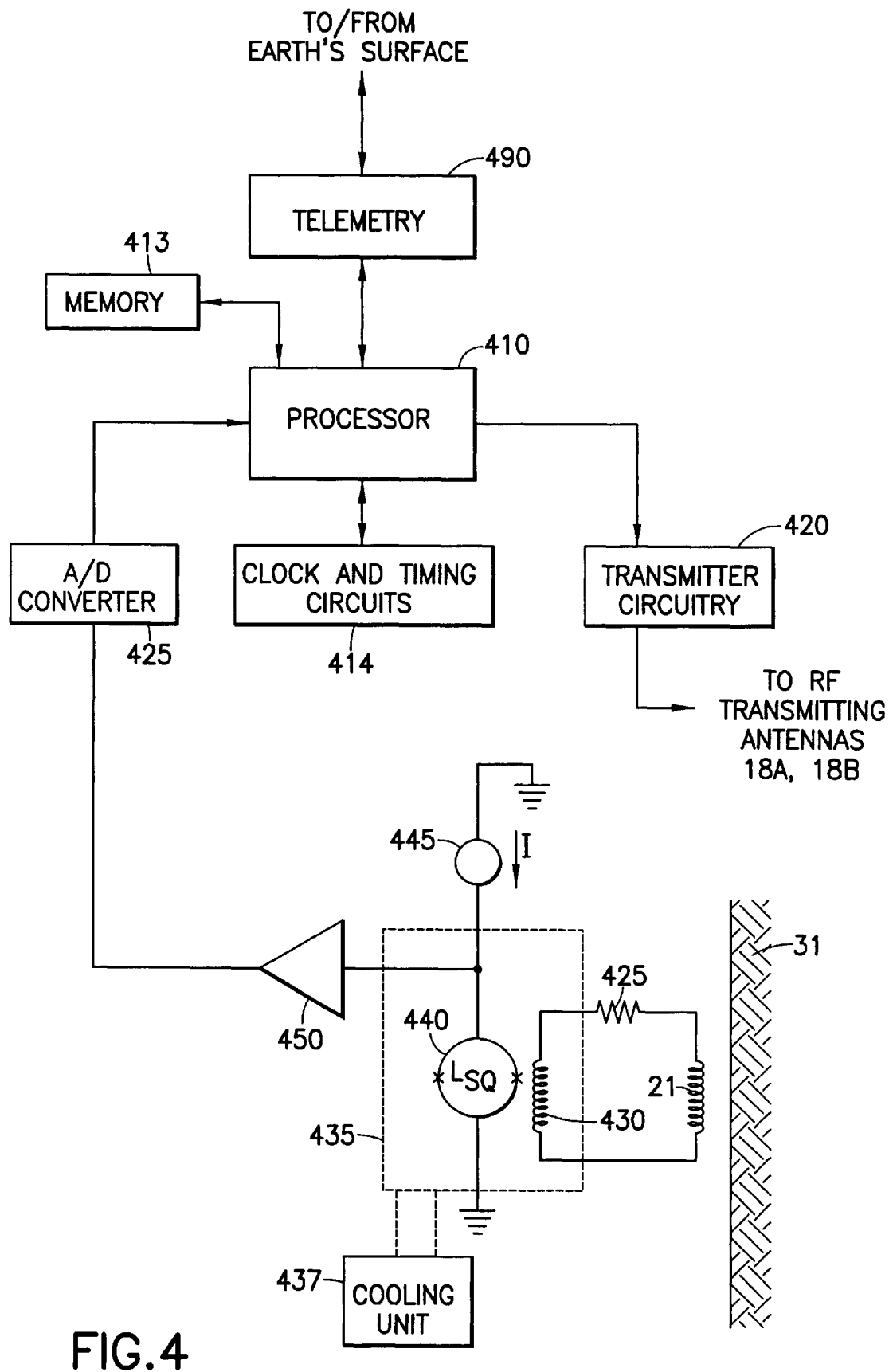
FIG. 4 is a block diagram of downhole circuitry in accordance with an embodiment of the invention.

FIG. 4 is a block diagram, partially in schematic form, of an embodiment of the downhole circuitry of logging device 30. A downhole processor subsystem can conventionally include a processor 410 (e.g. any suitable microprocessor) with associated memory 413 and clock/timing circuitry 414. Telemetry circuitry 490, coupled with the processor subsystem, is conventionally provided for communication with the earth's surface. Transmitter circuitry 420, under control of the processor subsystem, provides transmitter signals to RF antennas 18A and 18B. The transmitter circuitry can be of the general type disclosed in U.S. Pat. No. 5,055,787, and includes one or more oscillators and pulse formers which, in the present embodiment, are utilized in the generation of pulses of RF at the Larmor frequency in the volume of investigation (e.g., generally, region 9 in FIG. 1) for tipping the direction of the spins therein, preferably by 180 degrees. In the embodiment of FIG. 4, the pick-up loop antenna 21, shown adjacent formations 31, is part of an ambient temperature circuit that employs a SQUID. (Superconducting Quantum Intoferometric Device). [In the embodiment of FIG. 5, described subsequently, the pick-up antenna is in the cooled enclosure together with the SQUID.] In the FIG. 4 circuit, the pick-up coil 21 is coupled in a circuit having resistance 425 (the resistance of the wire, which is preferably minimized) and an input coil 430 of a SQUID 440. The input coil and SQUID are in a cooled enclosure 435 that is cooled by a cooling unit 437 that may be, for example, a liquid nitrogen cooling unit. A current source 445 provides input current to the SQUID 440, and the voltage across the SQUID, which is a measure of the sensed magnetic flux, is amplified by output amplifier 450. The amplified signal is coupled to analog-to digital converter 425, which samples under control of timing from processor 410 and whose output is, in turn, coupled to processor 410.

Figure 5:
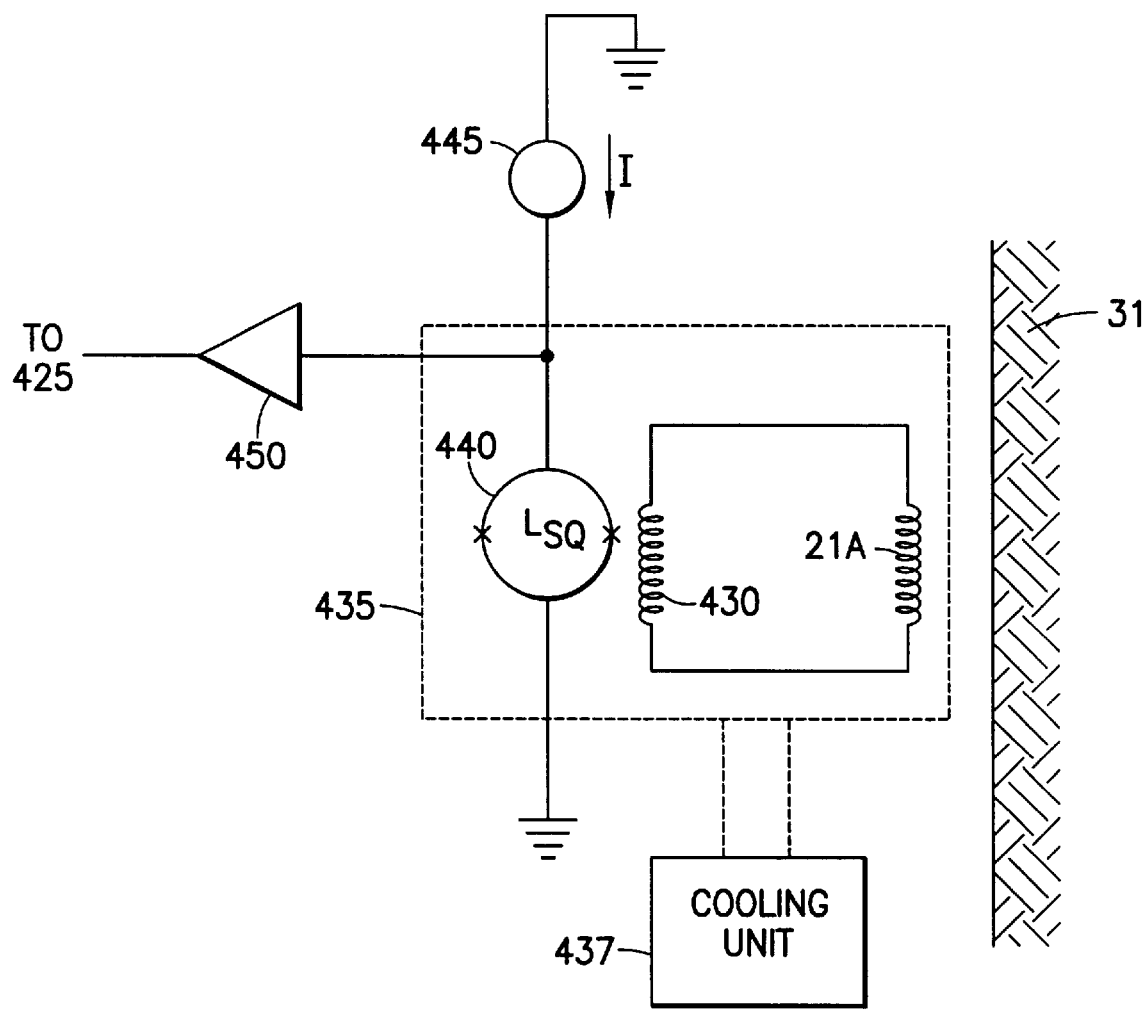
FIG. 5 is a block diagram of a portion of downhole circuitry in accordance with another embodiment of the invention.

In the embodiment of FIG. 5, the pick-up loop 21A is in the cooled enclosure (435A), together with the input loop 430A and the SQUID 440A. The enclosure can advantageously be a dewared all-metal enclosure. There is no resistance in the superconducting loop circuit. The output of amplifier 450 is then coupled to analog-to digital converter 455 (of FIG. 4).

In the embodiments of FIGS. 4 and 5, to cancel out time varying but spatially homogeneous fluxes, such as might be encountered by a tool moving in the earth's field, the pick-up loop can be a matched pair of loops connected in series opposition, with one loop being more sensitive to the formation than the other.

Referring to FIG. 6, there are shown graphs labeled 6A, 6B, and 6C, each as a function of time, which are useful in understanding the signals produced and detected when using embodiments of the present invention. The graph 6A represents the static magnetic field (assuming, for ease of illustration, that the logging device has moved into the investigation region at a time equals zero), the graph 6B represents the applied RF tipping pulse, and the graph 6C represents the magnetization (magnetic flux) sensed by the detection antenna 21 and associated circuitry. The graph 6A illustrates the static magnetic field, $B_0$, which, in the illustrated embodiments hereof, is produced by permanent magnets. In terms of a logging device moving through the borehole, the time t=0 can approximate the time that the logging device reaches a particular depth level at which the described logging measurements are to be made. After sufficient time for the spins in an investigation region to be polarized, an RF tipping pulse 615 is applied. For resonant operation, the RF is at the Larmor frequency of the spins (determined by the strength of the static magnetic field in the investigation region and the gyromagnetic ratio), and the duration of the pulse determines the tipping angle. In a preferred embodiment hereof, the tipping pulse is a 180 degree pulse. The graph 6C shows the magnetic field strength (magnetic flux) that is seen by the antenna 21. As the spins are initially polarized in the direction of the static field, the magnetic flux is seen to gradually build up (reference numeral 621). Then, the 180 degree RF pulse reverses the direction of magnetization of the spins, and thereby reverses the polarity of the magnetic field sensed by the detector, as seen at reference numeral 622 in the graph 6C. Then, in the region of the plot designated by reference numeral 623, the antenna 21 sees the magnetic field from of the spins as they gradually realign with the static field direction, with a characteristic longitudinal relaxation time constant $T_1$. The equation for magnetization M that defines the curve 623 is:

$$M = M_0(1 - 2e^{-t/T_1})$$

where $M_0$ is the magnetization of the polarized spins in the static field, and $T_1$ is the longitudinal relaxation time constant. It will be understood that for media having a distribution of $T_1$'s, the curve 623 will be a weighted sum of exponentials, with each exponential having a $T_1$ that is characteristic of the particular substance and a weighting coefficient that depends on the number of resonated spins in the particular substance. The points on the curve 623 (as illustrated generally in graph 6A) are representative digitized points that are sampled and input to the processor subsystem of FIG. 4 by analog-to-digital converter 425. The value of $T_1$ and/or the $T_1$ distribution can then be computed downhole, uphole, or at a remote location, using any suitable known technique, for example the type of technique disclosed in D. P. Gallegos and D. M. Smith, "A NMR Technique For The Analysis Of Pore Structure", Journal Of Colloid And Interface Science, 122, 143–153 (1988).

As first noted above, the RF tipping pulse will preferably be a 180 degree tipping pulse that will cause the spins to reverse direction. This will provide the maximum signal excursion ($2M_0$) for determination of $T_1$. However, it will be understood that operation can still be implemented if reversal is incomplete; that is for a tipping pulse of less or more than 180 degrees. [The tip angle depends on the RF pulse duration and magnitude. The rotation axis depends on the difference between the RF frequency and the Larmor frequency. Thus, a 180 degree tipping pulse for a given region of the formation will be a non-180 degree pulse in other formation regions where the magnitude of the static field is different.] The situation for a non-180 degree tipping angle, $\alpha$, is shown in graphs 7A, 7B, and 7C. The graph 7A again illustrates the static magnetic field, the graph 7B illustrates the RF tipping pulse (at, say, an angle $\alpha$ that is between 90 degrees and 180 degrees), and the graph 7C illustrates the magnetic field strength (magnetic flux) that is seen by antenna 21. In this case, if the field magnitude before tipping is again $M_0$, the field magnitude, $M$, in the longitudinal direction (static field direction) after tipping will be $$M = M_0(\cos \alpha)$$

and the exponential curve 723 will be in accordance with $$M = M_0[1-(1-\cos \alpha)e^{-t/T_1}].$$

As described so far, the magnetization of the spins is perturbed using an RF field with resonant operation, but it will be understood that alternative techniques can be employed. For example, if $B_0$ is changed (in either magnitude or direction), the magnetization will adjust to the new $B_0$ with the same time longitudinal relaxation time. For this general case we have $$M = \chi B_0$$

where $M$ (a vector) is the longitudinal nuclear magnetization, $B_0$ (a vector) is the applied magnetic field (from permanent magnets, current carrying coils, the earth, or a combination of those) and $\chi$ is the nuclear magnetic susceptibility. Thus, changing $B_0$ will change $M$, as shown in FIGS. 8A and 8B. If the time that the field is changed is $t=0$, then the equation for $M$ (for the case of a single exponential decay) is $$M = M_f + (M_i - M_f)\exp[-t/T_1] = \chi B_f + (\chi B_i - \chi B_f)\exp[-t/T_1]$$

where the subscript i represents initial value and the subscript f represents final value. This magnetization change (which can be growth or decay) can be sensed in the same manner as if an RF pulse had been applied, as previously described.

The two transmitting antennas of the present embodiment can be used to advantage as follows: When the sonde is moving up the borehole, the upper antenna can be energized to tip the spins in front of it. As the sonde moves, it carries the receiving antenna into close proximity to the tipped spins, which are in the process of recovering to their equilibrium state along the static field direction. If the tool is only used to log up, the lower antenna can be dispensed with. On the other hand, if the tool is used to log while descending, the lower antenna would be the one to be energized. When the tool is stopped (or moving very slowly) both antennas can be energized. In such case, neither tips the spins in front of the receiver very efficiently, but the fringing RF fields from both have some effect.

Figure 9:
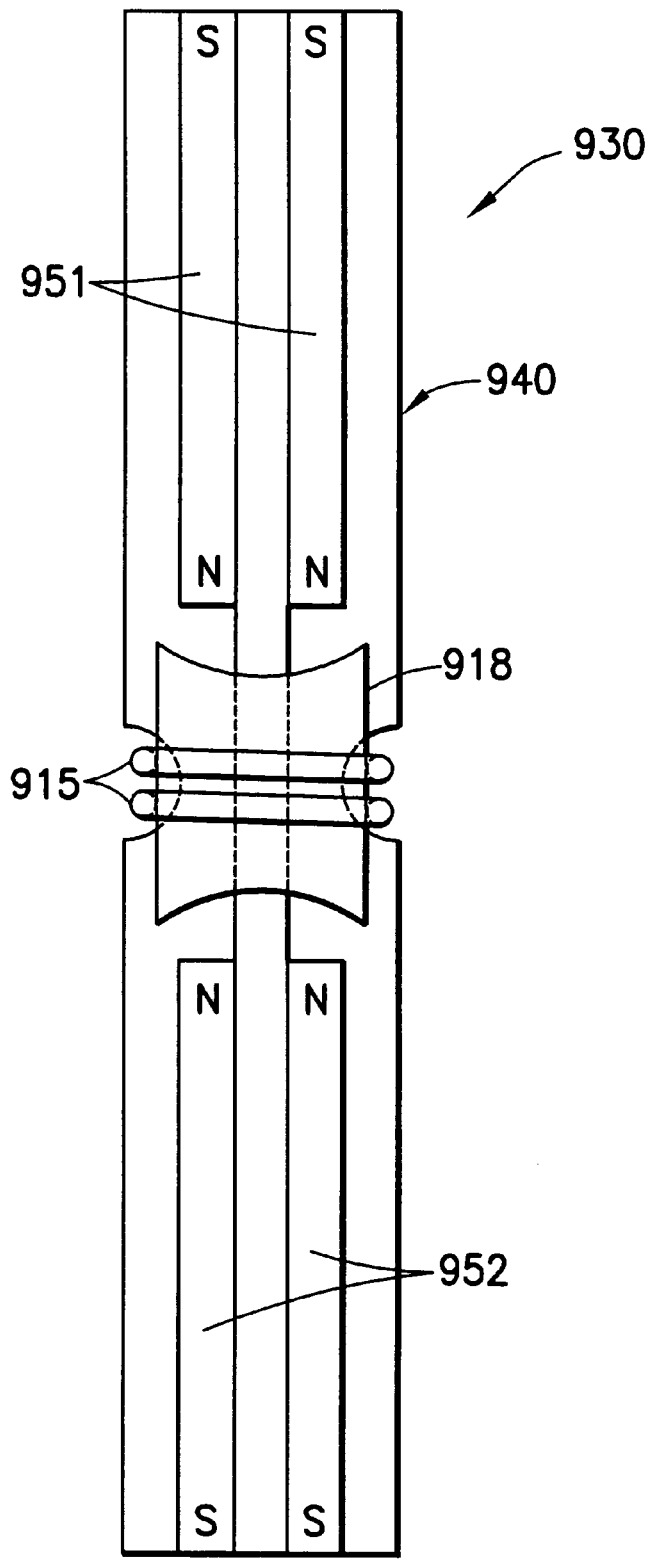
FIG. 9 is a cross-sectional view of an apparatus that can be used in practicing a further form of the invention.

FIG. 9 illustrates a further embodiment which utilizes a radial static field from opposing permanent magnets, as in J. Jackson, New NMR Well Logging/Fracture Mapping Technique With Possible Application Of SQUID NMR Detection, Soc. Of Explor. Geo., Tulsa, Okla., pp. 161–165, 1981. In this and other embodiments, the permanent magnets can be cooled (as in the reference). In the FIG. 9 embodiment, the logging device 930 has a body 940 that contains cylindric magnets 951, 952 of opposing polarity. The RF transmitting loop or coil 915 can be centrally located, as shown, in a recess in the logging device (or in a drill collar in a logging-while-drilling application). The axis of coil 915 is coincident with the tool axis and generally, with the borehole axis. One or more sensing loop antennas, each connected to a SQUID or another magnetic field flux detector, can be wound as a saddle coil (e.g. shown at 918) on the sonde so as to be sensitive to the changing radial magnetic field due to longitudinal nuclear spin relaxation. The apparatus may be rotating during the measurement if the measurement is made on a turning drill collar. In that case, an azimuthally resolved measurement can be made by correlating the instantaneous longitudinal magnetic signal with the rotation angle of the apparatus.

Existing superconductors will operate at or somewhat above liquid nitrogen temperature. In the absence of very large cooling powers it will be preferable to thermally shield the superconducting antenna with a vacuum dewar. This, in turn, necessitates the use of a metal structure that will not collapse under borehole pressure. For relatively low frequency measurements, such as those employed in the described embodiment, the pick-up loop can be located inside an all-metal enclosure such as a 0.25" titanium pressure housing. The frequency at which the housing constitutes one skin depth is about 30 kHz. For higher frequency operation, a section of the housing having a reduced wall thickness can be used. The stress on this section can be computed (see Marks, Standard Handbook For Mechanical Engineers, 8th Edition, Chapter 5) as:

$$St = wr^2/t^2$$

where w is the uniformly distributed load on a circular section, r is its radius, and t is its thickness. Taking w=20,000 psi and St=80,000 psi, which is the yield strength of titanium (see Marks, supra), then a ½" diameter section should be ⅛" thick. This is one skin depth at 130 kHz, and is appropriate for intermediate frequency measurements using superconducting sense coils.

The frequency selectivity of the metal housing which houses the receiver (but not the transmitter(s), which are outside the housing) is an advantage of embodiments of the invention. The frequency broadcast by the transmitting antenna(s) is at the Larmor frequency used to tip the spins, and is at a frequency (for example, 2 MHz) too high to penetrate metal housing walls of useful thickness. However, the magnetization decay of interest sensed by the receiver has a decay of the order of 0.1 msec or slower. A decay with a 0.1 msec time constant has spectral (Fourier) components in the frequency range between about 0 Hz and 10 kHz. For example, the 0.25 inch titanium pressure housing will easily pass the received signal, but not a 2 MHz transmitted pulse. Thus, since the receiver is completely shielded from the transmitted pulse, it will not be overloaded by the transmitted pulse. In contrast to existing NMR logging devices, there will be little or no receiver dead time, for example when operating the embodiment of FIG. 5.

The SQUID used in embodiments hereof can preferably be made with high $T_c$ superconductor, and can operate at or above the temperature of liquid nitrogen (77 K). Mechanical and thermophysical refrigerators are known which can maintain the cooled enclosure at temperatures needed to sustain superconductivity. Precooled thermal masses could also be employed.

What is claimed is:

1. A method for determining the nuclear magnetic resonance longitudinal magnetization decay of formations surrounding an earth borehole, comprising the steps of:

providing a logging device that is moveable through the borehole;

applying, from said logging device, a static magnetic field in the formations to align spins in the formations in the direction of the static magnetic field;

producing, from said logging device, an RF tipping pulse for tipping the direction of the spins with respect to the static magnetic field direction; and detecting, at said logging device, the time varying magnitude of the spin magnetization as said magnetization returns toward the static magnetic field direction;

said longitudinal magnetization decay being determinable from the detected time varying magnitude of the spin magnetization.

2. The method as defined by claim 1, further comprising determining the longitudinal relaxation time constant from said detected time varying magnitude of the spin magnetization.

3. The method as defined by claim 2, wherein said step of detecting the time varying magnitude of the spin magnetization includes providing a magnetic flux detection system.

4. The method as defined by claim 3, wherein said step of providing a magnetic flux detection system includes providing a magnetic flux detection antenna in an all-metal enclosure.

5. The method as defined by claim 4, wherein said step of providing a magnetic flux detection antenna in an all-metal enclosure further includes cooling said enclosure.

6. The method as defined by claim 5, further comprising providing a superconducting quantum interferometric device coupled with said magnetic flux detection antenna.

7. The method as defined by claim 5, wherein said detecting step comprises detecting spectral components in the range between about 0 Hz and 10 KHz.

8. The method defined by claim 5, wherein said step of providing a magnetic flux detection antenna within said all-metal enclosure comprises providing said antenna behind a section of said enclosure of reduced metal thickness.

9. The method defined by claim 4, wherein said step of providing a magnetic flux detection antenna within said all-metal enclosure comprises providing said antenna behind a section of said enclosure of reduced metal thickness.

10. The method as defined by claim 3, wherein said step of providing a magnetic flux detection system includes providing a magnetic flux detection antenna coupled with a superconducting quantum interferometric device.

11. The method as defined by claim 2, wherein said step of detecting the time varying magnitude of the spin magnetization comprises providing at said logging device a magnetic flux detection system which includes a magnetic flux detection antenna and a magnetic flux sensing circuit.

12. The method as defined by claim 11, wherein said step of providing a magnetic flux detection antenna includes providing a receiver coil.

13. The method as defined by claim 12, wherein said logging device has a longitudinal axis, and wherein the step of providing a receiver coil comprises providing a receiver coil having an axis that is perpendicular to said longitudinal axis.

14. The method as defined by claim 12, further comprising coupling said receiver coil with a superconducting quantum interferometric device.

15. The method as defined by claim 2, wherein said step of detecting the time varying magnitude of the spin magnetization comprises providing at said logging device a magnetic flux detection system, at least part of which is in a cooled enclosure.

16. The method as defined by claim 2, wherein said step of detecting the time varying magnitude of the spin magnetization includes providing a magnetic flux detection system for producing a number of output signals representative of successively sampled values of the magnetic flux over a period of time.

17. The method as defined by claim 2, wherein said determination of nuclear magnetic resonance relaxation time constant is implemented using only a single RF pulse.

18. The method as defined by claim 1, further comprising the step of determining the distribution of longitudinal time constants of said formations from the detected time varying magnitude of the spin magnetization.

19. The method as defined by claim 1, wherein said step of detecting the time varying magnitude of the spin magnetization includes providing a magnetic flux detection system.

20. The method as defined by claim 19, wherein said step of providing a magnetic flux detection system includes providing a magnetic flux detection antenna in an all-metal enclosure.

21. The method as defined by claim 20, wherein said step of providing a magnetic flux detection antenna in an all-metal enclosure further includes cooling said enclosure.

22. The method as defined by claim 21, further comprising providing a superconducting quantum interferometric device coupled with said magnetic flux detection antenna.

23. The method defined by claim 21, wherein said step of providing a magnetic flux detection antenna within said all-metal enclosure comprises providing said antenna behind a section of said enclosure of reduced metal thickness.

24. The method as defined by claim 4, wherein said detecting step comprises detecting spectral components in the range between about 0 Hz and 10 KHz.

25. The method as defined by claim 1, wherein said step of detecting the time varying magnitude of the spin magnetization comprises providing at said logging device a magnetic flux detection system, at least part of which is in a cooled enclosure.

26. The method as defined by claim 1, wherein said step of detecting the time varying magnitude of the spin magnetization comprises providing at said logging device a magnetic flux detection system which includes a magnetic flux detection antenna and a magnetic flux sensing circuit.

27. The method as defined by claim 26, wherein said step of providing a magnetic flux detection antenna includes providing a receiver coil.

28. The method as defined by claim 27, wherein said logging device has a longitudinal axis, and wherein the step of providing a receiver coil comprises providing a receiver coil having an axis that is perpendicular to said longitudinal axis.

29. The method as defined by claim 27, further comprising coupling said receiver coil with a superconducting quantum interferometric device.

30. The method as defined by claim 1, wherein said step of detecting the time varying magnitude of the spin magnetization includes providing a magnetic flux detection system for producing a number of output signals representative of successively sampled values of the magnetic flux over a period of time.

31. The method as defined by claim 1, wherein said step of producing an RF tipping pulse comprises producing a 180 degree tipping pulse.

32. Apparatus for determining the nuclear magnetic resonance longitudinal magnetization decay of formations surrounding an earth borehole, comprising:

a logging device that is moveable through the borehole;

means for applying, from said logging device, a static magnetic field in the formations to align spins in the formations in the direction of the static magnetic field;

means for producing, from said logging device, an RF tipping pulse for tipping the direction of the spins with respect to the static magnetic field direction; and means for detecting, at said logging device, the time varying magnitude of the spin magnetization as said magnetization returns toward the static magnetic field direction;

said longitudinal magnetization decay being determinable from the detected time varying magnetic field.

33. Apparatus as defined by claim 32, wherein said means for detecting, at said logging device, the time varying magnitude of the spin magnetization includes a magnetic flux detection system that includes a magnetic flux detection antenna coupled with a magnetic flux sensing circuit.

34. Apparatus as defined by claim 33, wherein said magnetic flux detection antenna comprises a flux detecting coil and said magnetic flux sensing circuit includes a superconducting quantum interferometric device.

35. Apparatus as defined by claim 34, wherein said magnetic flux sensing circuit includes an input coil coupled with said superconducting quantum interferometric device.

36. Apparatus as defined by claim 35, wherein said flux detecting coil is at ambient temperature, and wherein said input coil and said superconducting quantum interferometric device are contained in a cooled enclosure.

37. Apparatus as defined by claim 36, wherein said cooled enclosure is an all metal enclosure.

38. Apparatus ad defined by claim 37, wherein said detecting means is operative to detect spectral components in the range between about 0 Hz and 10 KHz.

39. Apparatus as defined by claim 33, wherein said magnetic flux sensing circuit includes a superconducting quantum interferometric device, and wherein said magnetic flux detection system is contained in a cooled enclosure.

40. Apparatus as defined by claim 39, wherein said cooled enclosure is an all metal enclosure.

41. Apparatus ad defined by claim 40, wherein said detecting means is operative to detect spectral components in the range between about 0 Hz and 10 KHz.

42. Apparatus as defined by claim 33, wherein said means for providing an RF tipping pulse comprises a pair of RF transmitting antennas longitudinally spaced apart on said logging device, and said flux detection sensor comprises a coil between said transmitting antennas.

43. Apparatus as defined by claim 42, wherein said logging device has a longitudinal axis, and wherein said magnetic flux detection antenna comprises a coil having an axis perpendicular to said longitudinal axis.

44. Apparatus as defined by claim 33, wherein said logging device has a longitudinal axis, and wherein said magnetic flux detection antenna comprises a coil having an axis perpendicular to said longitudinal axis.

45. Apparatus as defined by claim 33, wherein said logging device has a longitudinal axis, and wherein said means for providing a tipping pulse comprises a coil wound on said longitudinal axis and said magnetic flux detection antenna comprises at least one coil having an axis perpendicular to said longitudinal axis.

46. Apparatus as defined by claim 33, wherein said magnetic flux detection antenna is housed in an all metal enclosure, and said means for producing a tipping pulse includes a transmitting antenna outside said enclosure.

47. Apparatus as defined by claim 46, wherein said enclosure is a cooled enclosure.

48. Apparatus as defined by claim 47, wherein said magnetic flux sensing circuit includes a superconducting quantum interferometric device.

49. Apparatus as defined by claim 46, wherein said magnetic flux sensing circuit includes a superconducting quantum interferometric device.

50. A method for determining the nuclear magnetic resonance longitudinal magnetization decay of formations surrounding an earth borehole, comprising the steps of:

providing a logging device that is moveable through the borehole;

aligning spins in the formations in the direction of the static magnetic field;

perturbing, from said logging device, with an RF pulse, the magnetization of the spins; and detecting, at said logging device, the time varying magnitude of the perturbed spin magnetization;

said longitudinal magnetization decay being determinable from the detected time varying magnitude of the spin magnetization.

51. The method as defined by claim 50, further comprising determining the longitudinal relaxation time constant from said detected time varying magnitude of the spin magnetization.

52. The method as defined by claim 50, wherein said step of detecting the time varying magnitude of the spin magnetization includes providing a magnetic flux detection system, at least a portion of which is cooled.

53. The method as defined by claim 52, wherein said step of providing a magnetic flux detection system comprises providing a system that includes a magnetic flux detection antenna coupled with a magnetic flux sensing circuit.

54. The method as defined by claim 53, wherein said step of providing a magnetic flux sensing circuit includes providing a superconducting quantum interferometric device.

55. The method as defined by claim 52, wherein said step of providing a magnetic flux detection system includes providing said detection system in an all-metal enclosure, and operating said detecting system to detect spectral components in the range between about 0 Hz and 10 KHz.

* * * * *